United States Patent [19]

Skinner

[11] Patent Number: 4,873,991
[45] Date of Patent: Oct. 17, 1989

[54] BIOPSY NEEDLE

[76] Inventor: Bruce A. J. Skinner, 115 Upton Rd., Sauet Ste. Marie, Ontario, Canada, P6A 3W2

[21] Appl. No.: 247,169
[22] Filed: Sep. 21, 1988
[51] Int. Cl.$^4$ .............................................. A61B 10/00
[52] U.S. Cl. ...................................... 128/754; 128/305; 30/113.1; 30/280; 30/316
[58] Field of Search .................... 128/749, 751–754, 128/305, 310; 30/113.1, 278–281, 314–316, 347

[56] References Cited

U.S. PATENT DOCUMENTS

| | | | |
|---|---|---|---|
| 185,902 | 1/1877 | Fallows | 30/113.1 |
| 1,162,669 | 11/1915 | Vinnedge | 128/310 |
| 1,371,948 | 3/1921 | Szutz | 30/316 |
| 1,585,934 | 5/1926 | Muir | 128/754 |
| 1,977,017 | 10/1934 | Schiller | 30/301 |
| 2,198,319 | 4/1940 | Silverman | 128/754 |
| 2,263,531 | 11/1981 | Kevorkian | 30/301 |
| 2,843,135 | 7/1958 | Lisiewski | 30/316 |
| 3,007,471 | 11/1961 | McClure, Jr. | 128/754 |
| 3,577,979 | 5/1971 | van der Gaast | 128/2 |
| 3,683,892 | 8/1972 | Harris | 128/305 |
| 4,209,903 | 7/1980 | Owens | 30/302 |
| 4,600,014 | 7/1986 | Beraha | 128/754 |
| 4,649,918 | 3/1987 | Pegg et al. | 128/754 |
| 4,733,671 | 3/1988 | Mehl | 128/754 |

Primary Examiner—Max Hindenburg
Assistant Examiner—Randy Citrin
Attorney, Agent, or Firm—Price, Heneveld, Cooper, DeWitt & Litton

[57] ABSTRACT

A biopsy needle, for sampling tissue and the like, including a sidewall defining a hollow interior and a sharpened end. The needle has a lanced section which is formed from material of the sidewall itself and defines a rearwardly sloping, rearwardly facing blade disposed within the hollow interior of the needle. Tissue is sampled per insertion of the needle by severing the tissue with the sharpened end, passing the tissue into the hollow interior and slicing the tissue off by rotating the blade through 360 degrees. The sliced off sample is securely held by the blade as the needle is withdrawn.

14 Claims, 2 Drawing Sheets

BIOPSY NEEDLE

BACKGROUND OF THE INVENTION

The present invention relates to biopsy needles for sampling tissue and the like and, more particularly, to biopsy needles having a one-way valve arrangement allowing for secure removal of biopsy samples from a subject for histological assessment.

Through use of biopsy needles, most organs of a body can be biopsied with varying degrees of difficulty, danger and discomfort. While some organs of a subject patient can be biopsied with relative ease and minimal discomfort, using local anesthetic, skillful operation and use of general anesthetics are required to biopsy other organs. The degree of danger involved in the biopsy of a given organ is balanced against the benefits of having the tissue available for histological examination.

Due to a number of factors, such as the nature of the disease encountered in a given community and the incidence of that disease, some types of biopsies must be performed more frequently than others. For some diseases, it is sometimes necessary to obtain biopsies at intervals to follow the progress or regression of disease states. This is the case with liver disease and bone marrow disease.

Various problems may arise as a result of needle biopsy. First, due to the technical difficulty of retaining a biopsied specimen within the lumen of the needle, the quantity of tissue obtained is too small to be useful, and occasionally, no tissue is obtained at all. Second, damage to extracted tissue can occur because of mechanisms currently employed to retain tissue in the lumen of the needle during removal. Third the patient can be exposed to greater risk of damage when larger needles are employed. Finally, in the case of bone marrow biopsies, it is frequently necessary to rock the needle backwards and forwards, thus causing considerable discomfort for the patient.

Several needles have been introduced in the past for producing good-sized biopsy specimens suitable for histological assessment. The Menghini needle comprises a needle with a syringe on one end. The syringe is actuated so as to create negative pressure within the needle lumen as the needle is advanced into the tissue. The negative pressure is used to retain the biopsied specimen in the lumen of the needle as it is removed. The Menghini needle does not always perform its intended purpose, particularly in situations where the diseased tissue is very fibrous and hard. Additionally, the Menghini needle depends on considerable operator skill in order to provide proper and consistent use.

A Tru-cut needle is illustrated in Mehl U.S. Pat. No. 4,733,671 and Beraha U.S. Pat. No. 4,600,014. The Tru-cut needle includes a gutter drilled out of one end. As best illustrated in FIGS. 4-6 of the Beraha patent, a gutter penetrates the tissue such that the tissue falls into the gutter, so that as a metal sheath is passed over the opening of the gutter, a tissue sample is cut off. The Tru-cut needle tends to be rather large and needs considerable operator skill to produce consistently good samples.

The Vim Silverman needle, as best illustrated in Silverman U.S. Pat. No. 2,198,319 comprises a metal device split down the center with a natural inclination for two pieces to diverge from one another when pushed forward out of an accompanying sheath. Subsequent to penetrating tissue with the two pieces, the sheet is passed over the top of them, squeezing the tissue into place so that it can be withdrawn.

The Jamshidi needle is typically used for obtaining bone marrow biopsies. The needle comprises a hollow tube, one end of which is swaged to taper the end. As the tapered end penetrates bone marrow, a core of the tissue, having a diameter equal to the opening of the tapered end of the needle and less than the diameter of the body of the tube, passes into the lumen of the needle the tapered end of the needle is manipulated in order to cut off the cored tissue.

Russian Patent 553,970 discloses a biopsy instrument comprising a hollow needle having a sharpened end and a machined interior, rearwardly sloping and facing annular cutting ridge. Pegg et al. U.S. Pat. No. 4,649,918 is similar, in that it comprises a hollow needle with a bone cutting leading edge and three inwardly radiating machined teeth adjacent the cutting edge which occlude 10 to 20 percent of the cross-sectional area of the interior of the hollow needle. The needles in both of these references have to be machined in order to achieve the structure as shown. Further, it appears that there is a serious question as to how much of the specimen these two needles would retain in soft tissue, in that neither appears to occlude a considerable cross-sectional area of the interior of the needle.

SUMMARY OF THE INVENTION

The biopsy needle of the present invention has a lanced section which is formed from material of the sidewall itself and defines a rearwardly sloping, rearwardly facing blade disposed within the hollow interior of the needle. Tissue is sampled per insertion of the needle by severing the tissue with the sharpened end, passing the tissue into the hollow interior and slicing the tissue off by rotating the blade through 360 degrees. The sliced off sample is securely held by the blade as the needle is withdrawn.

DETAILED DESCRIPTION OF THE PREFERRED EMBODIMENTS

Figure 1:
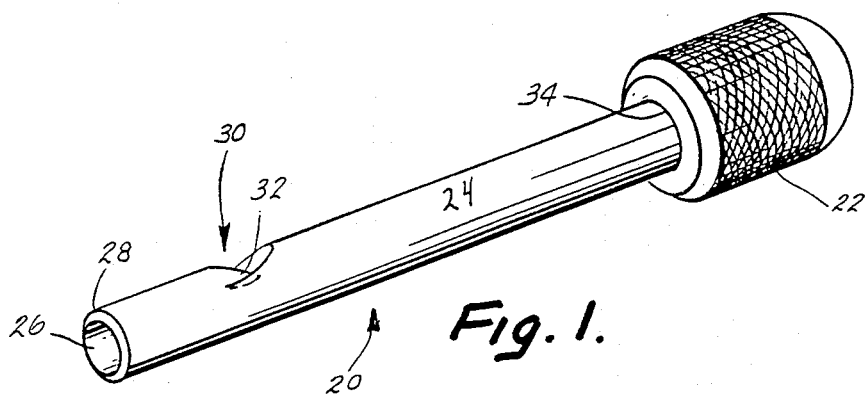
FIG. 1 is a perspective view of a biopsy needle, embodying the present invention, with a fitting attached thereto.

For purposes of description herein, the terms "upper," "lower," "right," "left," "rear," "front," "vertical," "horizontal" and derivatives thereof shall relate to the invention as oriented in FIG. 1. However, it is to be understood that the invention may assume various alternative orientations and step sequences, except where expressly specified to the contrary. It is also to be understood that the specific devices and procedure illustrated in the attached drawings, and described in the following specification, are simply exemplary embodiments of the inventive concepts defined in the appended claims. Hence, specific dimensions, and other physical characteristics relating to the embodiments disclosed herein are not to be considered as limiting, unless the claims by their language expressly state otherwise.

A biopsy needle 20 for sampling tissue and the like is illustrated in FIG. 1. Needle 20 projects from a fitting 22 and includes a sidewall 24, defining a hollow interior 26, as well as a sharpened end 28. The needle 20 has a lanced section 30 which is formed from material of sidewall 24 itself, and defines a rearwardly sloping, rearwardly facing blade 32 inside the hollow interior 26 of needle 20.

Biopsy needle 20 has a substantially circular cross section. Except at sharpened end 28 and lanced section 30, needle 20 is substantially uniformly sized throughout, defining lumen or hollow interior 26. In the presently envisioned best mode, the combined length of needle 20 and fitting 22 is about 10-20 cm and the needle diameter ranges from 2-6 mm. While smaller needles are desirable for biopsing, length and diameter of needle 20 varies according to sampling constraints.

Fitting 22 (FIG. 1) is disposed at an end 32, opposite sharpened end 28. In the preferred embodiment, fitting 22 is a plastic or metal handle which is used to manipulate and rotate needle 20 during the sampling process. Fitting 22 is attached to end 34 by conventional means, such as a threaded fitting or welding. An outside surface of fitting 22 is knurled for ease of handling and fitting 22 is adapted to allow flushing of tissue samples therethrough subsequent to removal of the same from a subject.

As is conventional with needles, sidewall 24, is preferably constructed from stainless steel. Sidewall 22 is relatively thin to maximize the amount of tissue sample that can be secured within hollow interior 26. The volume of hollow interior 26 should be great enough to contain a relatively good-sized biopsy specimen Sharpened end 28 of sidewall 24 (FIGS. 1 and 3) is typically beveled, using conventional means, such as machining. As would be expected by those skilled in the art, sharpened end 28 should be sharp enough to easily pierce either organs, bone marrow and the like for penetration of needle 20 therein.

Figure 2:
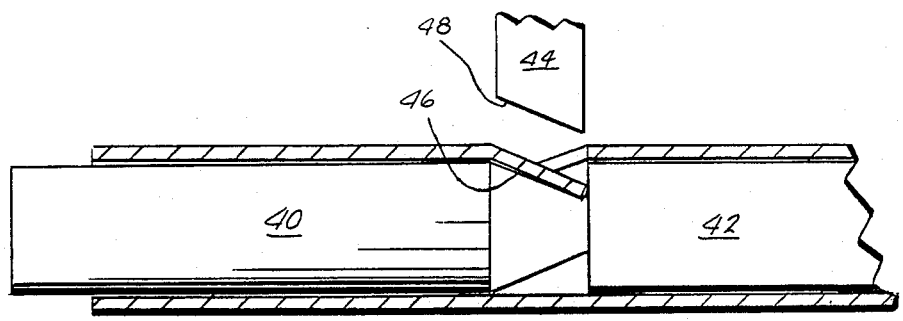
FIG. 2 depicts an arrangement, in fragmentary cross-sectional view, in which two dowels and a lance or punch are employed to lance the biopsy needle.

In the preferred embodiment, lanced section 30 (FIG. 3) is formed relatively near sharpened end 28. Typically, lanced section 30 is spaced rearward of sharpened end 28 so as to avoid deformation of sharpened end 28 as needle 20 is lanced. The method for forming lanced section 30 is best illustrated in FIG. 2. Lancing is effected through use of an arrangement including dowels 40 and 42 as well as lance 44. Dowels 40 and 42 are constructed to substantially fill hollow interior 26, so that sidewall 24 is optimally supported as needle 20 is impacted by lance 44.

Dowel 40 has a sloped surface 46 which is employed to control the depth to which blade 32 may be depressed. When dowels 40 and 42 are inserted into hollow interior 26, as shown in FIG. 2, and lance 44 is struck against sidewall 24, a portion of sidewall 24 is broken away and pressed downward unto sloping support surface 46. Upon removal of dowels 40 and 42, rearward sloping, rearward facing blade 32 remains.

Figure 3:
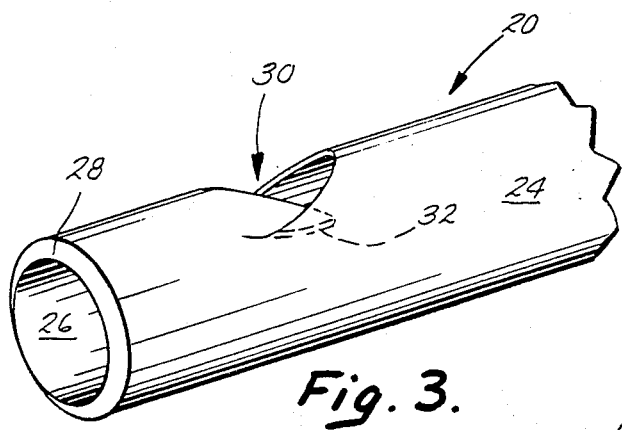
FIG. 3 is a fragmentary perspective view of the biopsy needle including a blade having the shape of a truncated parabola.
Figure 4:
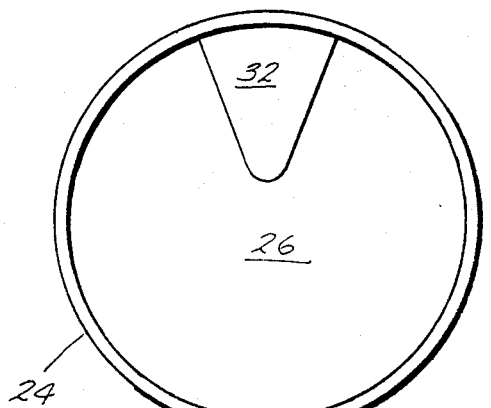
FIG. 4 is an end view of the biopsy needle shown in FIG. 3.

As best illustrated in FIGS. 3 and 4, blade 32 is depressed so that it occludes hollow interior 26. The preferred angle of inclination for blade 32 is about 30 degrees. In the preferred embodiment the vertical distance that blade 32 penetrates hollow interior 26, as measured from sidewall 24, is at least about 30% of the diameter of needle 20. Experimentation has indicated that such penetration provides the needle with at least two desirable attributes. First, pursuant to sampling, as needle 20 is rotated 360 degrees, at least 80% of the sample is sliced away from the tissue or marrow of the subject when vertical blade penetration is 30%. Second, 30% penetration facilitates a one-way valve arrangement. More specifically, as needle 20 is used to sample tissue, the same is passed by blade 32. After the sample is sliced off, a substantial portion of the same is secured rearward of blade 32. The occlusion of blade 32 within hollow interior 26 prevents the tissue sample from sliding back toward sharpened end 28.

Figure 8:
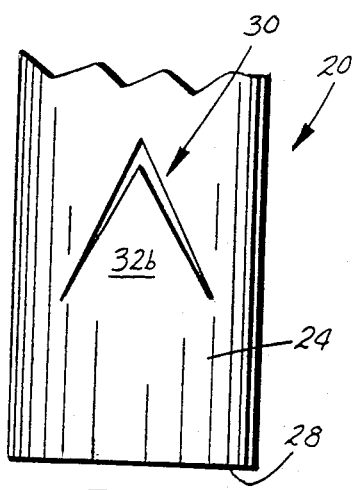
FIG. 8 is an overhead plan view of a biopsy needle having a triangularly shaped blade.
Figure 6:
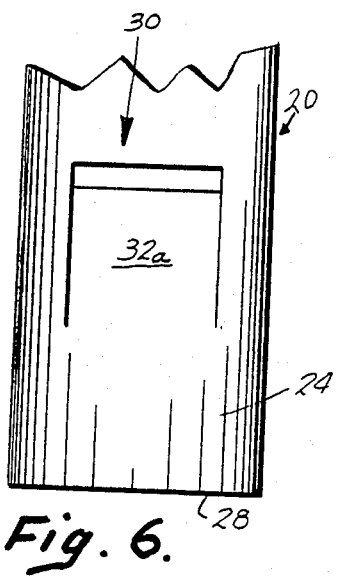
FIG. 6 is an overhead plan view of a biopsy needle having a rectangularly shaped blade.
Figure 5:
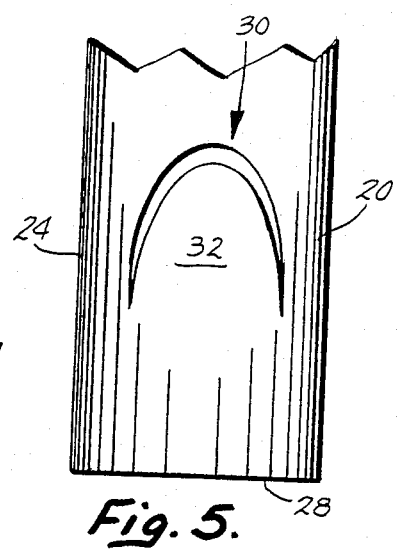
FIG. 5 is a overhead plan view of the biopsy needle depicted in FIG. 3.

As best illustrated in FIGS. 4–9, blade 32 may assume a variety of geometric shapes. In the present example, blade 32 assumes the shape of a truncated parabola. In other examples, however, the shape of blade 32 can be varied to yield a rectangularly-shaped blade 32a (FIG. 6) or a triangularly-shaped blade 32b (FIG. 8).

Figure 11:
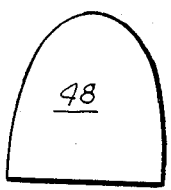
FIG. 11 shows the geometric shapes of alternative lance end surfaces.
Figure 11:
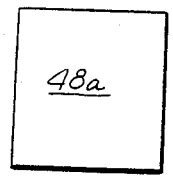
Figure 11:
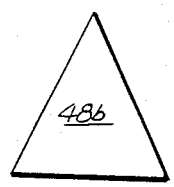

The shape of blade 32 is determined by the corresponding shape of a lower surface 48 of lance 44. That is, the shape of blade 32 will resemble the shape of lower surface 48. Accordingly, if lance lower surface 48 assumes the shape of a truncated parabola (FIG. 11), blade 32 (FIGS. 3 and 4) will result when sidewall 24 is lanced by lance 44.

Figure 10:
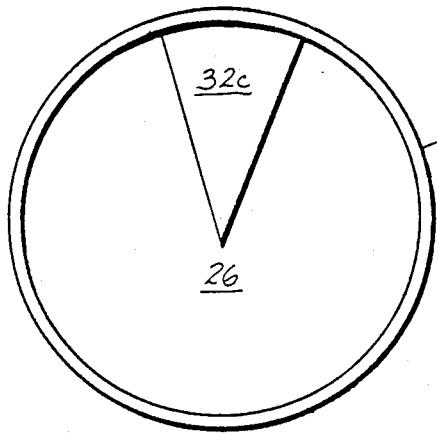
FIG. 10 is an end view of a biopsy needle similar to that shown in FIG. 8 except that the amount of occlusion is decreased by reducing the apical angle of the blade.
Figure 7:
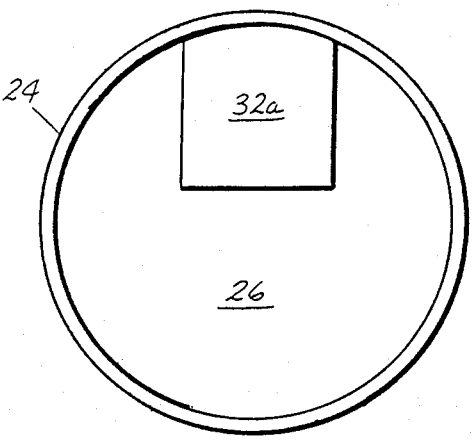
FIG. 7 is an end view of the biopsy needle depicted in FIG. 6.
Figure 9:
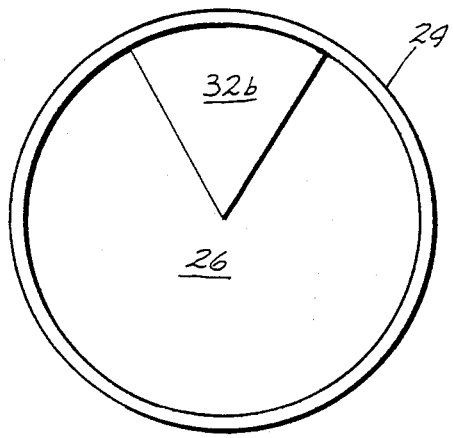
FIG. 9 is an end view of the biopsy needle depicted in FIG. 8.

Depending on the tissue or marrow being biopsied, it may be desirable to vary the dimensions of blade 32, 32a or 32b. For certain tissues, to facilitate passage of tissue samples past 32, 32a or 32b, it may be necessary to size down blade 32, 32a or 32b so that the area of occlusion within hollow interior 26 is decreased. Variation of blade occlusion may be visualized by comparing FIGS. 9 and 10. The needles of FIGS. 9 and 10 are the same except for the dimensioning of blades 32b and 32b'. Although blade 32b' has a vertical penetration that is the same as 32b, the apical angle of 32b' is less than hat of blade 32b so that the occlusion of 32b' is less than that of 32b. Blade 32b' impedes the ingress of tissue up hollow interior 26 less than that of 32b.

The one-way valve arrangement of the biopsy needle allows for convenient and secure sampling of tissue and the like. The simplicity of this arrangement eliminates much of the difficulty commonly associated with sampling. Due to the orientation of the blade relative to the sidewall, samples of sufficient quantity and quality may be easily collected.

The needle is easy to manufacture and can be produced for a relatively low cost. By varying the shape and size of the blade, the biopsy needle may be more effectively used in sampling various organs and bones. The biopsy needle is easy to use and is therefore particularly well-suited for its intended purpose.

In the foregoing description it will be readily appreciated by those skilled in the art that modifications may be made to the invention without departing from the concepts disclosed herein. Such modifications are to be considered as included in the following claims unless the claims by their language expressly state otherwise.

The embodiments of the invention in which an exclusive property or privilege is claimed are defined as follows.

1. A biopsy needle for sampling tissue and the like, said biopsy needle comprising:
   a sidewall of a rigid material defining a hollow interior portion;
   a sharpened forward end associated with said sidewall for severing the tissue;
   a lanced section disposed along said sidewall, said lanced section being formed from said rigid material of said sidewall itself and defining a rigid blade sloping and facing rearwardly away from said forward end and penetrating said hollow interior portion whereby upon inserting said needle into a subject, severing a tissue with said sharpened end, passing a tissue into said hollow interior and slicing off a tissue sample by rotating said blade 360 degrees, a tissue sample is securely held within said needle as said needle is withdrawn from a subject 2. The biopsy needle of claim 1, wherein:
   said lanced section is spaced a relatively short distance behind said sharpened forward end such that a majority of said needle hollow interior is devoted to retaining a tissue sample during removal from a subject while distortion of said needle in the vicinity of said sharpened end is minimized.

3. The biopsy needle of claim 2, wherein:
   said rearwardly sloping blade is inclined by an angle of about 30 degrees relative to said sidewall.

4. The biopsy needle of claim 3, wherein:
   said needle has circular cross section and said blade extends inwardly to a leading edge within said hollow interior of said needle; and
   said blade penetrates said hollow interior to an extend that the radial distance between said sidewall and said blade leading edge is at least 30% of the diameter.

5. The biopsy needle of claim 4, wherein:
   at the end opposite said sharpened forward end a fitting is operatively connected thereto for facilitating manipulation of said needle during tissue sampling.

6. The biopsy needle of claim 5, wherein:
   said blade has an overhead plan view resembling a truncated parabola.

7. The biopsy needle of claim 5, wherein:
   said blade has an overhead plan view resembling a rectangle.

8. The biopsy needle of claim 5, wherein:
   said blade has an overhead plan view resembling a triangle.

9. The biopsy needle of claim 1, wherein:
   said rearwardly sloping blade is inclined by an angle of about 30 degrees relative to said sidewall.

10. The biopsy needle of claim 1, wherein:
    said needle has a circular cross section and said blade extends inwardly to a leading edge within said hollow interior of said needle; and
    said blade penetrates said hollow interior to an extent that the radial distance between said sidewall and said blade leading edge is at least 30% of the diameter.

11. The biopsy needle of claim 1, wherein:
    at the end opposite said sharpened forward end a fitting is operatively connected thereto for facilitating manipulation during tissue sampling.

12. The biopsy needle of claim 1, wherein: said blade has an overhead plan view resembling a truncated parabola.

13. The biopsy needle of claim 1, wherein: said blade has an overhead plan view resembling a rectangle.

14. The biopsy needle of claim 1, wherein: said blade has an overhead plan view resembling a triangle.

* * * * *

UNITED STATES PATENT AND TRADEMARK OFFICE
CERTIFICATE OF CORRECTION

PATENT NO. : 4,873,991

DATED : October 17, 1989

INVENTOR(S) : Bruce A. J. Skinner

It is certified that error appears in the above-identified patent and that said Letters Patent is hereby corrected as shown below:

Column 1, line 68:
　"sheet" should read --sheath--;

Column 2, lines 29 and 30:
　"Summary of the Invention 30 The biopsy"
　should read --Summary of the Invention
　The Biopsy--;

Column 2, line 52:
　"a" should read --an--;

Column 4, line 53:
　"hat" should read --that--;

Column 6, claim 4, line 1:
　"extend" should read --extent--.

Signed and Sealed this

Twenty-eighth Day of January, 1992

Attest:

HARRY F. MANBECK, JR.

*Attesting Officer*　　　*Commissioner of Patents and Trademarks*